United States Patent
Li et al.

(10) Patent No.: US 11,912,657 B2
(45) Date of Patent: Feb. 27, 2024

(54) LOW SULFUR DIESEL BLOCKAGE INHIBITOR, PREPARATION METHOD THEREFOR AND USE THEREOF

(71) Applicants: CHINA PETROLEUM & CHEMICAL CORPORATION, Beijing (CN); SINOPEC DALIAN RESEARCH INSTITUTE OF PETROLEUM AND PETROCHEMICALS CO., LTD., Liaoning (CN)

(72) Inventors: Lanpeng Li, Liaoning (CN); Changhai Cao, Liaoning (CN); Jin Cheng, Liaoning (CN); Xiuzheng Li, Liaoning (CN); Yidi Wang, Liaoning (CN)

(73) Assignees: CHINA PETROLEUM & CHEMICAL CORPORATION, Beijing (CN); SINOPEC DALIAN RESEARCH INSTITUTE OF PETROLEUM AND PETROCHEMICALS CO., LTD., Liaoning (CN)

( * ) Notice: Subject to any disclaimer, the term of this patent is extended or adjusted under 35 U.S.C. 154(b) by 47 days.

(21) Appl. No.: 17/758,282

(22) PCT Filed: Dec. 31, 2019

(86) PCT No.: PCT/CN2019/130789
§ 371 (c)(1),
(2) Date: Jun. 30, 2022

(87) PCT Pub. No.: WO2021/134602
PCT Pub. Date: Jul. 8, 2021

(65) Prior Publication Data
US 2023/0039122 A1 Feb. 9, 2023

(51) Int. Cl.
*C07C 59/74* (2006.01)
*C07C 51/353* (2006.01)
(Continued)

(52) U.S. Cl.
CPC ............ *C07C 59/74* (2013.01); *C07C 51/353* (2013.01); *C10L 1/1881* (2013.01); *C10L 10/08* (2013.01);
(Continued)

(58) Field of Classification Search
CPC ... C07C 59/74; C07C 51/353; C07C 2601/16; C07C 51/487; C10L 1/1881; C10L 10/08;
(Continued)

(56) References Cited

U.S. PATENT DOCUMENTS 6,239,298 B1 * 5/2001 Williamson .......... C10L 1/1963
44/418
2009/0113788 A1 * 5/2009 Reaney .................... C10L 1/18
44/308
(Continued)

FOREIGN PATENT DOCUMENTS

CA 2112732 C 2/2004
CA 2628059 A1 10/2007
(Continued)

OTHER PUBLICATIONS

Zhu, Linfeng et al., "Reasons and Solutions for Blockage of Diesel Pipeline", Anhui Chemical Industry, vol. 39, No. 6, Dec. 31, 2013, pp. 30-32.
(Continued)

*Primary Examiner* — Ellen M McAvoy
(74) *Attorney, Agent, or Firm* — NKL Law; Allen Xue

(57) ABSTRACT

A low sulfur diesel blockage inhibitor as shown in formula (I), a preparation method therefor, and use thereof are
(Continued)

provided. In formula (I), x and y are each an integer between 0 and 4; m and n are each selected from H, a C1-C6 linear or branched alkyl group, or a C3-C6 cycloalkyl group. By using a vegetable oil as a raw material, a modified vegetable oil fatty acid is first obtained, and then a polar group of an unsaturated dialdehyde with a certain chain length is introduced into a molecular chain of the modified vegetable oil fatty acid.

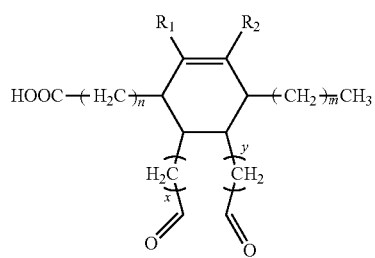

Formula (I)

20 Claims, 7 Drawing Sheets

(51) Int. Cl.
*C10L 1/188* (2006.01)
*C10L 10/08* (2006.01)
*C10M 129/93* (2006.01)
*C11C 3/14* (2006.01)
*C10N 40/25* (2006.01)

(52) U.S. Cl.
CPC ............. *C10M 129/93* (2013.01); *C11C 3/14* (2013.01); *C07C 2601/16* (2017.05); *C10M 2207/40* (2013.01); *C10N 2040/252* (2020.05)

(58) Field of Classification Search
CPC ...... C10L 2230/083; C10L 2200/0446; C10M 129/93; C10M 2207/40; C10M 129/40; C11C 3/14; C11C 3/00; C10N 2040/252; Y02E 50/10
USPC ............................................ 508/516; 44/410
See application file for complete search history.

(56) References Cited

U.S. PATENT DOCUMENTS

2020/0095514 A1* 3/2020 Liu ..................... C10L 1/1905
2023/0151290 A1* 5/2023 Lin ......................... C10L 10/08
44/398

FOREIGN PATENT DOCUMENTS

| CN | 103666603 A | 3/2014 |
| CN | 108219874 A | 6/2018 |
| CN | 109486537 A | 3/2019 |
| CN | 109486538 A | 3/2019 |
| CN | 109576021 A | 4/2019 |
| CN | 109576063 A | 4/2019 |
| RU | 2515238 C2 | 10/2014 |

OTHER PUBLICATIONS

Jin, Yulin et al., "Effects of three antiwear agents on the total No. of bacterial colonies in 0# diesel", China Petrochem, Jun. 30, 2017, vol. 39, pp. 211-212.

Nurmuhammad et al., "Synthesis of C22-Tribasic Acid", Speciality Petrochemicals, vol. 23, No. 2, Mar. 31, 2006, pp. 25-26.

Kuzmichev, V.I. et al.; "Water-Soluble Film-Formers and Paint and Varnish Materials Based On Them"; Moscow; 1986, pp. 19-20.

* cited by examiner

LOW SULFUR DIESEL BLOCKAGE INHIBITOR, PREPARATION METHOD THEREFOR AND USE THEREOF

TECHNICAL FIELD

The invention pertains to the technical field of bio-based blockage inhibitors, and particularly relates to a compound useful as a vegetable oil based blockage inhibitor and a preparation method thereof, a vegetable oil based blockage inhibitor and a preparation method and a use thereof, as well as a low sulfur diesel blockage inhibitor containing the vegetable oil based blockage inhibitor and a low sulfur diesel using the blockage inhibitor.

BACKGROUND ART

The consumption of diesel fuel has been increasing year by year along with the widespread use of diesel engines. However, the large consumption of diesel fuel inevitably leads to further increase of harmful substances discharged from vehicles. Since the emission of harmful substances have imposed serious impacts on the ecological environment, human health and economic development, the governments in various countries have successively enacted strict emission regulations, limiting the hazardous waste emissions of diesel vehicles. According to the implemented national-V standard in China with respect to emission of diesel, the content limit value of sulfur in diesel will be reduced to below 10 ppm, the requirements of desulfurized diesel have been implemented in the domestic refineries. At present, the sulfur reduction technologies such as hydrotreating and hydrocracking are adopted in China, such that the sulfur content of fuel oil is greatly reduced, however, the content of polar compounds in diesel is excessively low, thus the lubricity of diesel is significantly reduced, the abrasion and damage phenomena of a large number of diesel pumps occur, the blockage problem of filter screen and nozzle of an engine frequently appears, thereby shortening the service life of the diesel pumps.

In order to solve the problem of abrasion and damage to the diesel pumps, the antiwear agents are generally added into diesel fuel. The currently available antiwear agents on the market mainly comprise unsaturated fatty acids, unsaturated fatty acid esters and amide derivatives thereof, wherein the acid type antiwear agents dominate about 70% of the market, the ester type antiwear agents and the amide type antiwear agents account for about 30% of the market.

The lubricity problem of diesel can be desirably solved by adding vegetable oleic acid into low sulfur diesel. However, the vegetable oleic acid mostly contains a certain amount of saturated fatty acid with a high condensation point; because the boiling point of the saturated fatty acid is close to that of the vegetable oleic acid, it is difficult to complete separate the saturated fatty acid from the vegetable oleic acid by using the existing separation means, such as a freezing squeezing method and/or a distillation refining method, so that the condensation point of the vegetable oleic acid on the market is generally higher than −8° C., and the use standard of the acid type blockage inhibitor with the condensation point not higher than −12° C. specified in the enterprise standard Q/SHCG 57-2014 "lubricity Additive for Diesel Fuels" specified by the Sinopec Group cannot be achieved.

Moreover, the antiwear agent cannot desirably solve the problem that the oil supply is insufficient due to the blockage of filter screen and nozzle of an engine, so that an oil atomizer is abraded and the engine fails, the service life of a diesel pump is shortened. Therefore, it is required to further research and develop a blockage inhibitor product suitable for low sulfur diesel.

SUMMARY OF THE INVENTION

For the sake of solving the defects in the prior art, the invention provides a vegetable oil based blockage inhibitor, a preparation method and an use thereof. The vegetable oil based blockage inhibitor prepared by the invention has the advantages of low condensation point, low acid value, low blending ratio, desired lubricity and the like, and the blended blockage inhibitor product can meet the requirements of lubricity and the condensation point specified by the national-V standard of China.

In a first aspect, the present invention provides a compound represented by Formula (I):

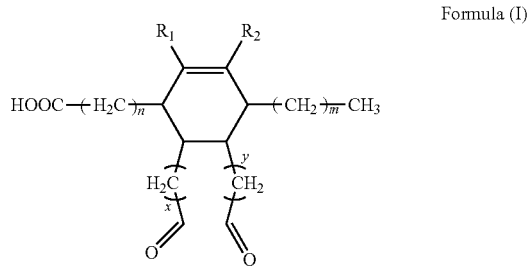

Formula (I)

wherein x and y are each an integer between 0 and 4; m and n are each an integer between 3 and 9, and 10≤m+n≤14; $R_1$ and $R_2$ are respectively selected from H, a C1-C6 linear or branched alkyl group or a C3-C6 cycloalkyl group.

Preferably, m=4 or m=5, and m+n=12.

Preferably, x and y are each independently 0 or 1. The values of x and y are the same or different.

Preferably, $R_1$ and $R_2$ are respectively selected from H, methyl or ethyl. $R_1$ and $R_2$ are the same or different.

In a second aspect, the present invention provides a use of the compound as a vegetable oil based blockage inhibitor.

In a third aspect, the present invention provides a method for preparing a vegetable oil based blockage inhibitor, wherein the method comprises the following steps:

(1) subjecting a non-conjugated vegetable oil to a haptoreaction with an alkali or an alcohol solution of an alkali under isomerization reaction condition;

(2) acidifying and washing a product obtained from the haptoreaction, and then separating out an aqueous phase to obtain a modified vegetable oil fatty acid;

(3) contacting the modified vegetable oil fatty acid with an unsaturated dialdehyde under Diels-Alder addition reaction condition;

(4) removing unreacted raw materials to obtain a vegetable oil based blockage inhibitor.

Preferably, the non-conjugated vegetable oil of step (1) is a vegetable oil having non-conjugated carbon-carbon double bonds and a linolenic acid content not more than 0.6% and an iodine value not less than 60 mgKOH/g, preferably not less than 85 mgKOH/g; the non-conjugated vegetable oil is preferably one or more selected from the group consisting of corn oil, cottonseed oil, peanut oil, sesame oil and shinyleaf yellowhorn oil.

Preferably, wherein the alkali in step (1) is potassium hydroxide and/or sodium hydroxide with an used amount being 0.5-0.6 times of the non-conjugated vegetable oil by mass; the alcohol is saturated dihydric alcohol, preferably C2-C5 saturated dihydric alcohol, preferably at least one of ethylene glycol, 1,3-propanediol and 1,4-butanediol, and the used amount of said alcohol is 2.5-3.5 times of the non-conjugated vegetable oil by mass.

Preferably, the isomerization reaction conditions in step (1) comprise a temperature of 180-220° C. and a time of 3-5 hours.

Preferably, the unsaturated dialdehyde in step (3) has 4-12 carbon atoms, preferably one or more selected from the group consisting of 2-butene dialdehyde, 2-pentene dialdehyde, 2-hexene dialdehyde, 3-hexene dialdehyde, 2-heptene dialdehyde, 3-heptene dialdehyde, 2-octene dialdehyde, 3-octene dialdehyde and 4-octene dialdehyde, the molar ratio of unsaturated dialdehyde to vegetable oil fatty acid is preferably 0.5:1-3:1, more preferably 0.8:1-2:1.

Preferably, the contacting time in the step (3) is 0.5-2 h, and the temperature is preferably 190-210° C.

Preferably, the mode of removing the unreacted raw materials comprises subjecting the mixture obtained from the contacting process to a reduced pressure distillation under a pressure of 30-150 Pa, preferably 65-120 Pa, and a temperature of 180-220° C., preferably 195-205° C.

In a fourth aspect, the present invention further provides a vegetable oil based blockage inhibitor prepared with the aforementioned preparation method of vegetable oil based blockage inhibitor, and a low sulfur diesel blockage inhibitor composition comprising the vegetable oil based blockage inhibitor.

Preferably, the low sulfur diesel blockage inhibitor composition comprises 70-90 wt % of vegetable oil based blockage inhibitor, 0.2-2 wt % of antioxidant, and 8-29 wt % of aromatic hydrocarbon solvent oil, based on the total amount of the low sulfur diesel blockage inhibitor composition. Preferably, the low sulfur diesel fuel blockage inhibitor composition is consisting of a vegetable oil based blockage inhibitor, an antioxidant and an aromatic hydrocarbon solvent oil.

In a fifth aspect, the present invention further provides a low sulfur diesel with improved blockage inhibition property, comprising a low sulfur diesel and a blockage inhibitor, wherein the blockage inhibitor is the aforementioned vegetable oil based blockage inhibitor or the low sulfur diesel blockage inhibitor composition.

Preferably, the content of said vegetable oil based blockage inhibitor (i.e., the compound represented by Formula (I) or a combination of two or more compounds thereof) is 0.008-0.01 parts by weight relative to 100 parts by weight of low sulfur diesel.

In a sixth aspect, the present invention also provides a method for improving low sulfur diesel blockage inhibition property, wherein the method comprises adding the aforementioned compound, or the vegetable oil based blockage inhibitor, or the low sulfur diesel blockage inhibitor composition into the low sulfur diesel.

Preferably, the content of said vegetable oil based blockage inhibitor (i.e., the compound represented by Formula (I) or a combination of two or more compounds thereof) is 0.008-0.01 parts by weight relative to 100 parts by weight of low sulfur diesel.

The present invention uses a vegetable oil as a raw material, and firstly obtains a modified vegetable oil fatty acid, and then introduces a polar group of unsaturated dialdehyde with a certain chain length into a molecular chain of the modified vegetable oil fatty acid, such that the obtained product can desirably solve the problem of the blockage of an engine filter nozzle, reduce the number of engine failures, improve the service life of an engine, and reduce the usage amount of a blockage inhibitor The reason may be that the molecule comprises two aldehyde groups and one carboxyl, which not only increases the molecular polarity, but also the aliphatic ring structure is conducive to reducing the intermolecular binding action, can solve the problem of breeding bacteria in diesel fuel, and avoids the phenomena of breeding bacteria and causing the blockage of the filter by bacteria excrement in diesel after long-term storage. In addition, the compound also has lubricity, and compared with the existing acid type low sulfur diesel antiwear agent, the product has lower condensation point and acid value, exhibits better lubricating effect, reduces the blending ratio, avoids the corrosion to diesel engines, and is particularly suitable for the use in cold regions.

The performance indicators of the vegetable oil based blockage inhibitor prepared by the invention, such as condensation point, flash point, metal content, low-temperature storage stability, can meet the lubricity requirements specified in the national-V standard of China. The invention has the characteristics of simple and convenient technological process, readily available raw materials, low cost, and easy for industrial production.

DETAILED DESCRIPTION OF PREFERRED EMBODIMENTS

Figure 1:
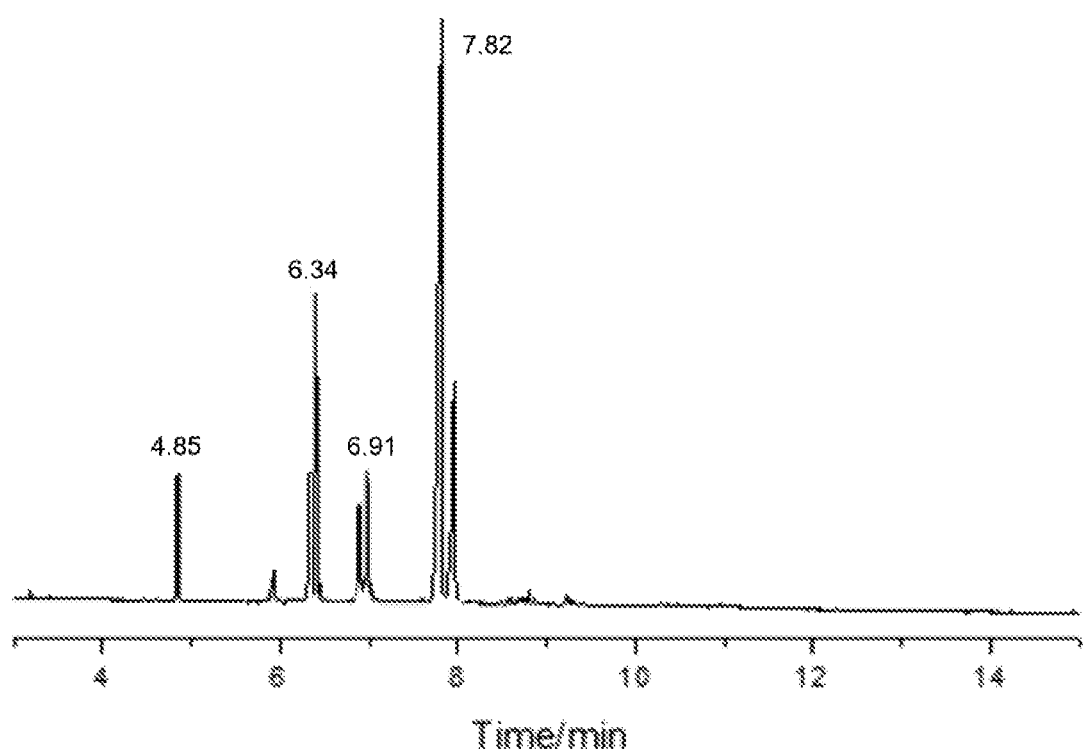
FIG. 1 and FIG. 2 illustrate the Hydrogen Nuclear Magnetic Resonance spectrogram of the modified soybean oil fatty acid obtained in step (1) and the blockage inhibitor product obtained in step (2) of Example 1 of the invention, respectively.

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

In the present invention, the non-conjugated vegetable oil refers to a vegetable oil containing non-conjugated double bonds, wherein it comprises various saturated fatty acids and unsaturated fatty acids, for example, a linear or branched fatty acid having 12-22 carbon atoms. Preferably, the unsaturated fatty acid content is not less than 70 wt. %, preferably not less than 75 wt. %, based on the total amount of non-conjugated vegetable oil. The saturated fatty acid is, for example, stearic acid and/or palmitic acid. The unsaturated fatty acid refers to a fatty acid containing unsaturated double bonds, the number of said unsaturated double bonds may be one, two, three or more, preferably, the number of the unsaturated double bonds in the non-conjugated vegetable oil is 2-5, such as one or more selected from the group consisting of oleic acid, linoleic acid and linolenic acid. Preferably, the content of fatty acid comprising two or more unsaturated double bonds is not less than 40 wt. % based on the total amount of the non-conjugated vegetable oil; the content of linoleic acid is more preferably 40-70 wt. %, more preferably 45-65 wt. %. The content of conjugated double bond unsaturated fatty acids (e.g., alpha-eleostearic acid) is less than 60 wt. %, preferably less than 50 wt. %, further preferably less than 40 wt. %, based on the total amount of non-conjugated vegetable oil.

In the present invention, the contents of various saturated fatty acids and unsaturated fatty acids are measured by a gas chromatography method.

In the present invention, the content of oleic acid, linoleic acid, stearic acid and the like in the non-conjugated vegetable oil can be determined by subjecting the non-conjugated vegetable oil to a gas chromatography and comparing the non-conjugated vegetable oil with standard samples such as oleic acid, linoleic acid, stearic acid, and the number of unsaturated double bonds can be further determined with reference to the number of unsaturated double bonds of various fatty acids.

Preferably, the iodine value of the non-conjugated vegetable oil is 60-155 mg ($I_2$) (100 g)$^{-1}$, preferably 85-130 mg ($I_2$) (100 g)$^{-1}$.

Preferably, the acid value of the non-conjugated vegetable oil is 180-210 mg (KOH) g$^{-1}$, preferably 190-200 mg (KOH) g$^{-1}$.

In the present invention, the acid value and iodine value of the non-conjugated vegetable oil are measured according to the methods in the national standards GB/T5530-2005 and GB/T5532-2008 of China, respectively.

Preferably, the non-conjugated vegetable oil has a molecular weight of 700-1,000, preferably 850-950.

Since the types of vegetable oil fatty acids in nature are known among those skilled in the art, and the people have already separated different fatty acids thoroughly. Those skilled in the art may be aware of the fatty acid composition of the non-conjugated vegetable oil by obtaining the gas chromatograms of various fatty acid standard samples in advance and then comparing the gas chromatograms of said non-conjugated vegetable oil with various fatty acid standard samples, so as to obtain the (average) molecular weight of the non-conjugated vegetable oil. The invention used said method to obtain the molecular weight of the non-conjugated vegetable oil.

In the present invention, the non-conjugated vegetable oil is preferably one or more selected from the group consisting of corn oil, cottonseed oil, peanut oil, sesame oil and shinyleaf yellowhorn oil.

In the present invention, the alkali in step (1) may be any of various alkaline substances capable of providing an environment for isomerization reaction, and is preferably potassium hydroxide and/or sodium hydroxide. The used amount of said alkali is preferably 0.5-0.6 times the mass of the non-conjugated vegetable oil.

In the present invention, the non-conjugated vegetable oil may be directly subjected to isomerization reaction in the presence of an alkali. According to a preferred embodiment of the invention, the alkali is used in the form of an alcohol solution of the alkali. Preferably, the alcohol is a saturated dihydric alcohol, further preferably a saturated dihydric alcohol having 2-7 carbon atoms, more preferably a saturated dihydric alcohol having 2-4 carbon atoms, and particularly preferably at least one of ethylene glycol, 1,3-propanediol, and 1,4-butanediol. The used amount of the alcohol is preferably 2.5-3.5 times the mass of the non-conjugated vegetable oil.

In the step (1), the non-conjugated vegetable oil, the inorganic alkali and the optionally contained dihydric alcohol are mixed and stirred for reaction at the temperature of 160-180° C. for 3-5 hours. The stirring rate is preferably 100-500 rpm, and more preferably 300-400 rpm. The reactor may be a conventionally used reactor with stirring function, it is preferable to automatically control the temperature, pressure, stirring speed and the like.

In the present invention, the acidification in step (2) is preferably performed to a pH of 2-3 by using an inorganic acid, which may be at least one of hydrochloric acid, sulfuric acid and nitric acid.

In the present invention, the washing process is preferably performed by using distilled water, deionized water and the like, until the wash water is neutral, and the aqueous phase is separated after standing still and layering.

Through the step (1), at least a part of the non-conjugated double bonds in the non-conjugated unsaturated fatty acids in the non-conjugated vegetable oil can be converted into conjugated double bonds by isomerization. The generation of reaction can be verified through the nuclear magnetic resonance and the infrared detection methods.

In the present invention, the unsaturated dialdehyde in step (3) is unsaturated dialdehyde having 4-12 carbon atoms, preferably one or more selected from the group consisting of 2-butene dialdehyde, 2-pentene dialdehyde, 2-hexene dialdehyde, 3-hexene dialdehyde, 2-heptene dialdehyde, 3-heptene dialdehyde, 2-octene dialdehyde, 3-octene dialdehyde and 4-octene dialdehyde.

The aforementioned unsaturated dialdehydes are commercially available or prepared with known methods, for example, 2-pentene dialdehyde can be prepared by reacting cyanogen bromide with the pyridine ring to convert nitrogen atom on the ring from tri-valent nitrogen atom to 5-valent nitrogen atom, and subjecting the pyridine ring to a hydrolysis reaction to obtain pentene dialdehyde; alternatively, the thiocyanate reacts with chloramine T to generate cyanogen chloride, which then reacts with isonicotinic acid and subjects to hydrolysis to generate pentene dialdehyde (refer to CHEN Hui-zhu, et al, "Determination of thiocyanate in milk and dairy products by spectrophotometry", *Chinese Journal of Health Laboratory technology*, 2012(08): 46-48). 3-hexene dialdehyde can be prepared through oxidation of 3-hexene-1,6-diol (commercially available) with a copper catalyst. 4-octene dialdehyde can be obtained from oxidation of 1,5-cyclooctadiene. The above-mentioned specific methods are well known among those skilled in the art and will not be repeated herein.

According to a preferred embodiment of the invention, the molar ratio of unsaturated dialdehyde to vegetable oil fatty acid (total amount of the unsaturated fatty acid and the saturated fatty acid) is 0.5:1-3:1, preferably 0.8:1-2:1.

In step (3) of the present invention, the modified vegetable oil fatty acid and the unsaturated dialdehyde are put into a reactor and subjected to reaction for 0.5-2 h at the temperature of 180-220° C., preferably 190-210° C.

Preferably, the contacting of step (3) is performed under ultrasonic conditions, and more preferably, the entire contacting process of step (3) is performed under ultrasonic conditions. The ultrasonic power is preferably 100 W-600 W, more preferably 200-300 W.

In the step (3), the conjugated unsaturated double bond in the unsaturated fatty acid and the unsaturated bond in the unsaturated dialdehyde subject to a Diels-Alder addition reaction, and cyclization to obtain a compound having a structure represented by the Formula (I). The generation/existence of the compound with a structure represented by Formula (I) can be verified by Gas Chromatography, TOFF Mass Spectrometry, Infrared Spectroscopy, Hydrogen Nuclear Magnetic Resonance Spectrometry and Carbon Nuclear Magnetic Resonance Spectrometry. For example, the formation of a new characteristic peak in gas chromatography can demonstrate the occurrence of a reaction, and in combination with the TOFF Mass Spectrometry, the molecular weight information of a new compound formed by the reaction can be obtained; Infrared Spectroscopy can be used for deducing and learning the reaction mechanism and the specific functional group of the new compound formed by the reaction; the molecular weight information of TOFF Mass Spectrometry and the functional group information of Infrared Spectroscopy are utilized in combination with the results of Hydrogen Nuclear Magnetic Resonance Spectrometry and Carbon Nuclear Magnetic Resonance Spectrometry, so that the product molecular structure of the new compound formed by the reaction can be obtained.

In the present invention, the unreacted raw materials in the mixture obtained after the reaction in step (3) can be removed through various modes, and preferably through the reduced pressure distillation. Preferably, the reduced pressure distillation is performed under a pressure of 30-150 Pa, more preferably 65-120 Pa, and a temperature of 180-220° C., more preferably 195-205° C. Unless otherwise specified in the present invention, the pressure refers to an absolute pressure.

It should be noted that, because of the high stereoselectivity of the Diels-Alder addition reaction, a mixture of two isomers is obtained by the above method, and the two isomers have proximate chemical shifts and similar polarities, and the same molecular weight, thus the two isomers usually exist in a form of a mixture. Unless otherwise specified in the present invention, the compound represented by the Formula (I) or the vegetable oil based blockage inhibitor is exactly a mixture of two isomers.

In a third aspect, the invention further provides a low sulfur diesel blockage inhibitor containing the vegetable oil based blockage inhibitor, which mainly comprises 70-90 wt % of vegetable oil based blockage inhibitor, 0.2-2 wt % of antioxidant, and 8-29 wt % of aromatic hydrocarbon solvent oil.

The antioxidant may be various substances with oxidation resistance suitable for the diesel blockage inhibitor, and a phenolic antioxidant is generally selected. The phenolic antioxidant may be monophenol, bisphenol, diphenol and polyphenol, or a mixture thereof in any proportion. Such as o-tert-butylphenol, p-tert-butylphenol, 2-tert-butyl-4-methylphenol, 6-tert-butyl-2-methylphenol, 6-tert-butyl-3-methylphenol; 4-tert-butyl-2,6-dimethylphenol, 6-tert-butyl-2,4-dimethylphenol; 2,4-di-tert-butylphenol, 2,5-di-tert-butylphenol, 2,6-di-tert-butylphenol; 2,5-di-tert-butyl-4-methylphenol, 2,6-di-tert-butyl-4-methylphenol (BHT, antioxidant T501), 4,6-di-tert-butyl-2-methylphenol; 2,4,6-tri-tert-butylphenol, 2-allyl-4-methyl-6-tert-butylphenol, 2-sec-butyl-4-tert-butylphenol, 4-sec-butyl-2,6-di-tert-butylphenol, 4-nonyl-2,6-di-tert-butylphenol, 2,6-di-tert-butyl-4-ethylphenol (antioxidant DBEP), 2,6-di-tert-butyl-4-n-butylphenol (antioxidant 678); 2(3)-tert-butyl-4-hydroxyanisole (BHA), 2,6-di-t-butyl-alpha-methoxy-p-cresol (BHT-MO), 4-hydroxymethyl-2,6-di-t-butylphenol (antioxidant 754), 2,6-di-t-butyl-alpha-dimethylamino-p-cresol (antioxidant 703), 4,4'-isopropylidenebisphenol (bisphenol A), 2,2'-bis-(3-methyl-4 hydroxyphenyl) propane (bisphenol C), 4,4'-dihydroxybiphenyl (antioxidant DOD), 4,4'-dihydroxy-3,3', 5,5'-tetra-t-butylbiphenyl (antioxidant 712), 2,2'-methylene-bis-(4-methyl-6-t-butylphenol) (antioxidant bisphenol 2246), 4,4'-methylene-bis-(2-methyl-6-tert-butylphenol) (antioxidant methylene 736), 2,2'-methylene-bis-(4-ethyl-6-tert-butylphenol) (antioxidant 425), 2,2'-methylene-bis-(4-methyl-6-cyclohexylphenol) (antioxidant ZKF), 2,2'-methylene-bis[4-methyl-6-(alpha-methylcyclohexyl)phenol] (antioxidant WSP), 2,2'-methylene-bis-(6-alpha-methylbenzyl-p-cresol), 4,4'-methylene-bis-(2,6-di-tert-butylphenol) (antioxidant T511), 4,4'-methylene-bis-(2-tert-butylphenol) (antioxidant 702), 2,2'-ethylene-bis-(4-methyl-6-tert-butylphenol) (antioxidant 2246), 4,4'-butylene-bis-(6-tert-butyl-m-cresol) (antioxidant BBM, antioxidant TCA) and the like.

In the present invention, low sulfur diesel refers to the diesel fuel having a sulfur content less than 10 ppm.

When the compound represented by Formula (I) provided by the invention is used for improving the blockage inhibition property of the low sulfur diesel, the compound can be directly added into the low sulfur diesel base oil, or can be compounded with other additives such as an antioxidant to form a blockage inhibitor Formula (composition) and then added into the low sulfur diesel, in order to obtain the low sulfur diesel with the improved blockage inhibition property.

In the present invention, for the sake of differentiation, the diesel before and after the addition of said blockage inhibitor are denoted as the low sulfur diesel and the low sulfur diesel with improved blockage inhibition property, respectively. The improved blockage inhibition property means that the blockage inhibition property of said diesel is improved regardless of the magnitude of the improvement, compared with the diesel before an addition of the blockage inhibitor.

The vegetable oil-based low sulfur diesel blockage inhibitor and the preparation method and application effect thereof are further described below with reference to examples. The examples are implemented under the premise of the technical scheme of the invention, and provide the detailed embodiments and specific operation processes, but the protection scope of the invention is not limited to the following examples.

Unless otherwise specified, each of the experimental methods in the following examples pertains to the conventional methods in the art. All the reagents are commercially available products or prepared with the conventional methods.

The acid value of the blockage inhibitor product prepared by the invention was measured according to the method specified in the national standard GB/T7304 of China, the condensation point was determined according to the method specified in the national standard GB/T510 of China, and the wear scar diameter (corresponding to the lubricity) of low sulfur diesel was measured according to the method specified in the petrochemical industry standard SH/T0765 of China.

Conversion rate of vegetable oil fatty acids $A=(m_1-m_2)/m_1 \times 100\%$. Wherein $m_1$ denoted the mass of the vegetable oil fatty acid charged in the second step of reaction; $m_2$ denoted the mass of vegetable oil fatty acid separated after the reaction.

The equipment models and analysis conditions adopted by the Gas Chromatography test were as follows: the samples were prepared according to the national standard GB/T17376 "Animal and vegetable fats and oils—Preparation of methyl esters of fatty acids" of China; the instrument was Thermo DSQ II, and the chromatographic column was Agilent DB-1 HT; the conditions were as follows: the initial temperature was 170° C., the temperature was maintained for 1 min, the temperature was increased to 350° C. at the temperature rise rate of 5° C./min, the temperature was then maintained for 5 min, the temperature of a sample inlet was 260° C., the temperature of a detector was 280° C., the split ratio was 20:1, and the sample injection volume was 1 μL.

In the present invention, the equipment models and analysis conditions adopted by Infrared Spectroscopy were as follows: the instrument was Thermo NICOLET 6700; the condition was $CaF_2$ coating, the scanning range was 400-4,000 cm$^{-1}$, the resolution was 4 cm$^{-1}$, and the scanning number was 32 times.

The equipment model and the analysis conditions adopted by the Hydrogen Nuclear Magnetic Resonance Spectrogram analysis were as follows: the instrument was Bruker AVANCE III 500 model; the conditions were as follows: the test temperature was 300K, the resonance frequency (SFO1) was 500 MHz, the solvent was deuterated chloroform, the interior label was tetramethylsilane, the Spectral Width (SWH) was 10,000 Hz, the pulse width (P1) was 10 μs, the sampling time was 3.27 s, the number of sampling (NS) was 64 times, and the delay time (D1) was 10 s.

The equipment model and the analysis conditions adopted by the Carbon Nuclear Magnetic Resonance Spectrogram analysis were as follows: the instrument was Bruker AVANCE III 500 model; the conditions were as follows: the test temperature was 300K, the resonance frequency (SFO1) was 125 MHz, the solvent was deuterated chloroform, the interior label was tetramethylsilane, the Spectral Width (SWH) was 10,000 Hz, the pulse width (P1) was 10 μs, the sampling time was 3.27 s, the number of sampling (NS) was 64 times, and the delay time (D1) was 10 s.

The equipment model and analysis conditions adopted by the TOF mass spectrometry in the invention were as follows: the instrument was a Bruker microfex matrix-assisted laser desorption ionization time-of-flight mass spectrometer; the conditions were as follows: dithranol (dithranol, 20 mg/mL) and sodium trifluoroacetate (10 mg/mL) were dissolved in tetrahydrofuran to prepare a solvent for use. The matrix was α-cyano-4-hydroxycinnamic acid (HCCA), the HCCA was dissolved into said solvent and subjected to an to an ultrasonic dissolution to prepare a saturated solution, which was centrifuged for standby; a sample to be detected was dissolved into the solvent (10 mg/mL), a polypeptide solution and a matrix solution supernatant with equal volume were taken and uniformly blended, 1 μL of the mixed solution was then dropwise added onto a sample plate for natural drying and crystallization. The crystal was then sent to a mass spectrometer for analysis. The detection was performed by adopting a cation reflection mode, wherein the reflection voltage was 19 kV The single scanning signal was transmitted for 200 times to obtain a mass spectrogram, the baseline correction and peak marking were performed by using the built-in analysis software of said instrument.

Example 1

(1) 1,000 g of corn oil (with an iodine value of 125 mgKOH/g and other properties shown in the following Table 1), 3,500 g of ethylene glycol and 600 g of KOH were put into a reactor and uniformly mixed, and subjected to stirring and reaction at 160° C. for 5 hours, the product was acidified by hydrochloric acid until the pH was 2.5, and then washed with water to be neutral, the product was subjected to standing still and layering to separate out an aqueous phase, thereby obtaining the modified corn oil fatty acid.

(2) 100 g of modified corn oil fatty acid and 44.5 g of 2-butene dialdehyde (also known as maleic dialdehyde, the manufacturer was Shanghai Jinjinle industrial Co., Ltd., the purity was 99%, the product described below was the same) were taken and added into an ultrasonic wave reactor, the compounds were subjected to stirring at 300 rpm and reaction for 1 h under the reaction temperature of 130° C. and the ultrasonic power of 200 W to finish the reaction; after the reaction system was cooled to room temperature, the reduced pressure distillation was performed, the fractions generated under the temperature of 200° C. and a pressure of 65 Pa were collected to obtain a blockage inhibitor product. The conversion rate of the corn oil fatty acid was 48.2%, the product had an acid value of 122.5 mgKOH/g and a condensation point of −26.5° C.

Figure 2:
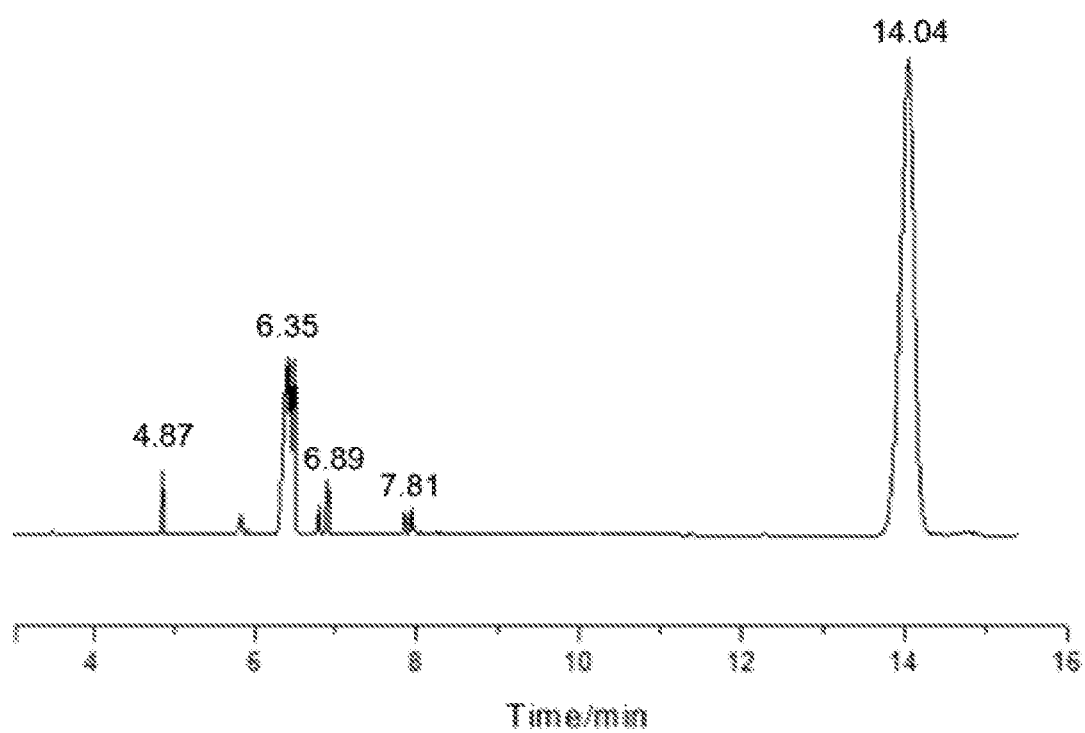

FIG. 1 and FIG. 2 illustrated the gas chromatograms of the modified corn oil fatty acid and the product which was not separated after the cycloaddition reaction, respectively; as can be seen, the characteristic peak of the target product appeared at the run-time of 14.04 min after the cycloaddition reaction, and the characteristic peak representing the modified corn oil fatty acid disappeared at the run-time of about 7.8 min, it proved that the Diels-Alder addition reaction occurred in the system.

Figure 3:
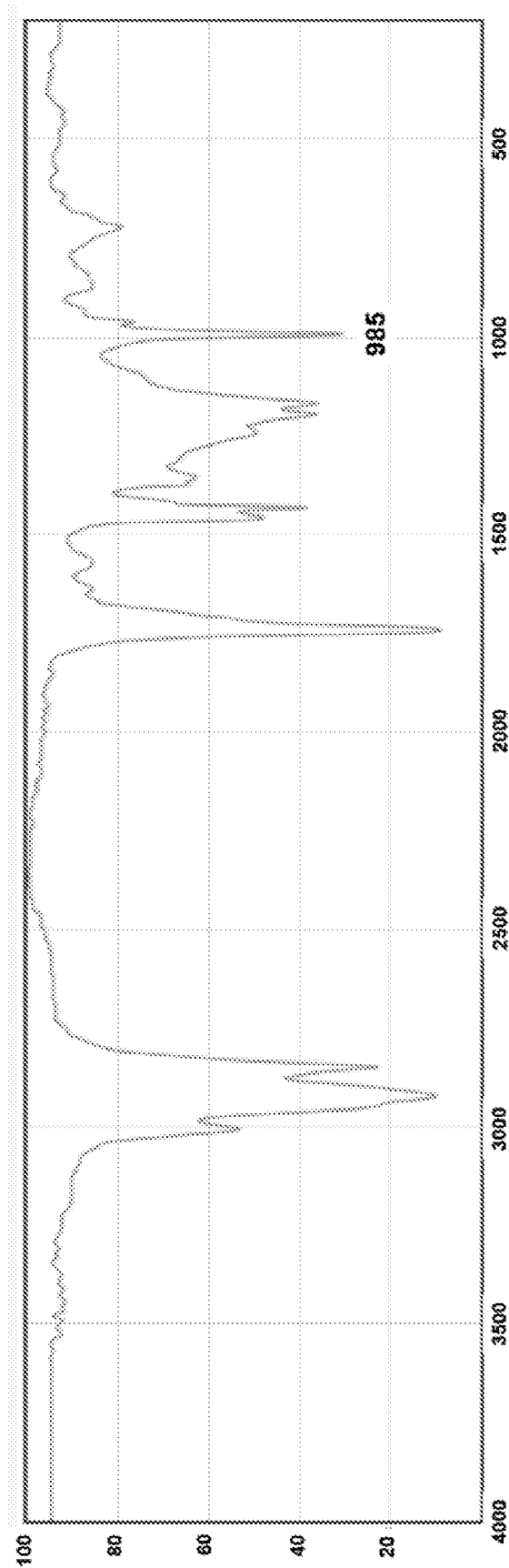
FIG. 3 and FIG. 4 illustrate the Infrared Spectrogram of the modified soybean oil fatty acid obtained in step (1) and the blockage inhibitor product obtained in step (2) of Example 1 of the invention, respectively.
Figure 4:
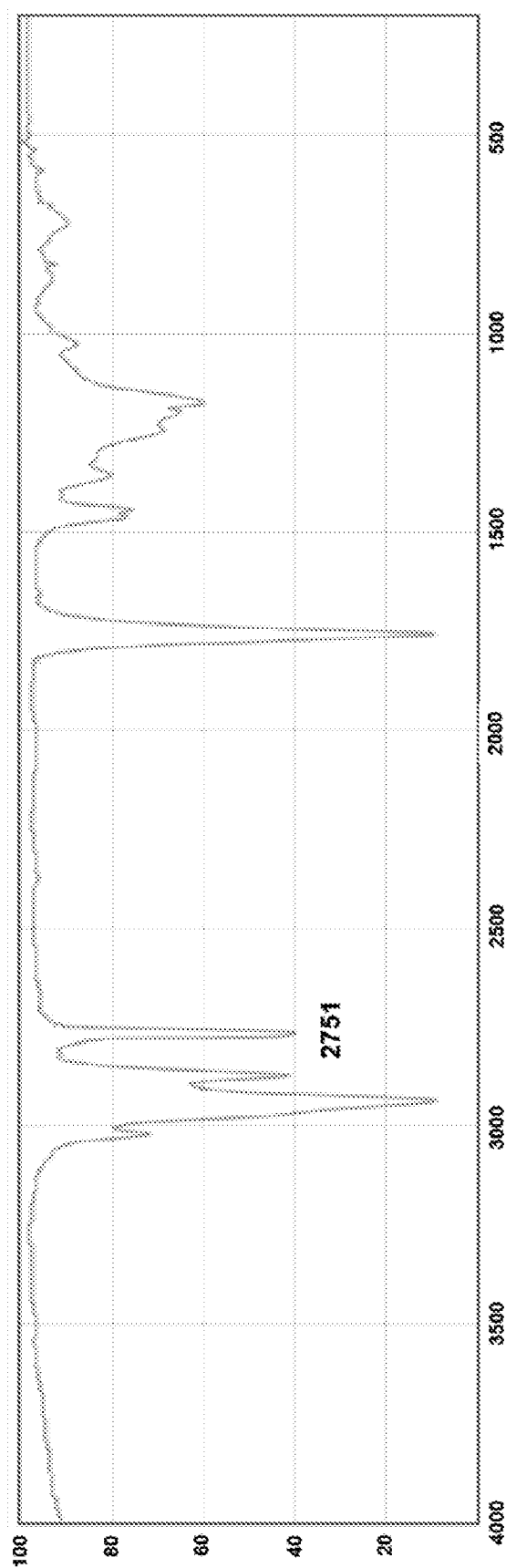

FIG. 3 and FIG. 4 illustrated the infrared spectrogram of the modified corn oil fatty acid and the product obtained after separation, respectively, wherein the absorption peak at 985 cm$^{-1}$ was the characteristic peak of the carbon-carbon conjugated double bond, the absorption peak at 2,751 cm$^{-1}$ was the characteristic peak of the aldehyde group, it can be determined that the reacted product comprised the aldehyde group functional group, in addition, the characteristic peak of the carbon-carbon conjugated double bond substantially disappeared, it proved that the aldehyde group was successfully introduced into the molecular chain of the modified corn oil fatty acid through the Diels-Alder addition reaction.

Figure 5:
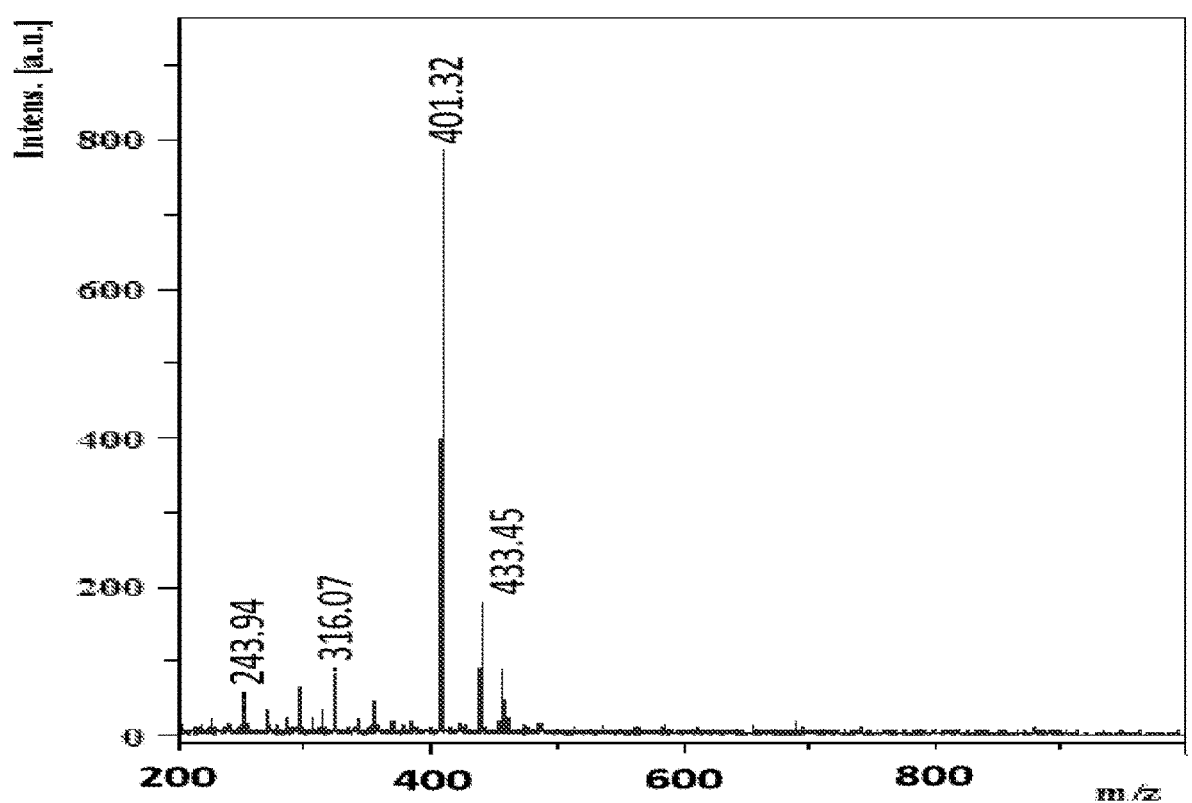
FIG. 5 shows a TOF mass spectrogram of the blockage inhibitor prepared in Example 1.

FIG. 5 illustrated the TOF mass spectrogram of the prepared blockage inhibitor, it can be judged that the product had a molecular weight of 364. It may be determined that the product had a carboxyl functional group in the product molecule with reference to the acid value 122.5 mgKOH/g of the product and the molecular weight of said product.

Figure 6:
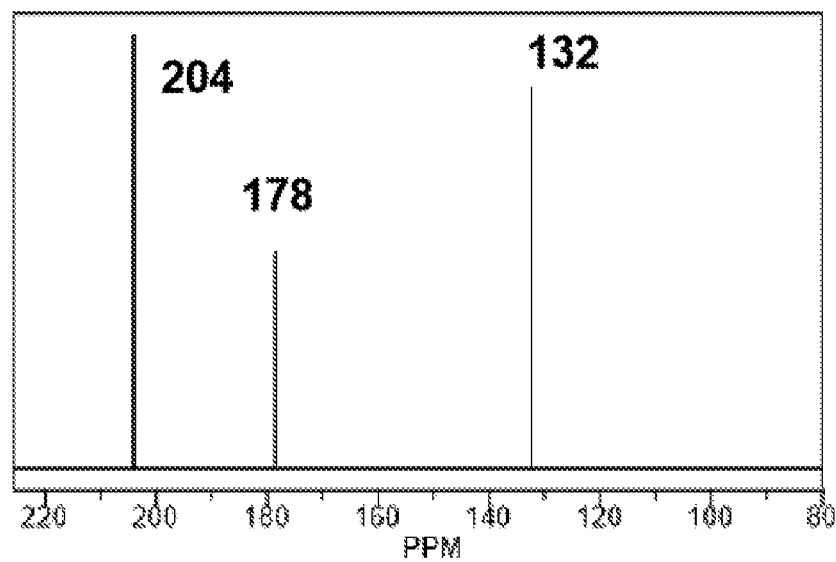
FIG. 6 illustrates a Carbon Nuclear Magnetic Resonance ($^{13}$C-NMR) spectrogram of the blockage inhibitor prepared in Example 1.

FIG. 6 illustrated a Carbon Nuclear Magnetic Resonance ($^{13}$C-NMR) spectrogram of the prepared blockage inhibitor, wherein the chemical shift of δ=178 ppm assigned to the carbon in carboxyl group; the chemical shift of δ=204 ppm assigned to the carbon in aldehyde group; the chemical shift of δ=132 ppm assigned to the carbon in the carbon-carbon double bond. According to the absorption peak intensity, the number of aldehyde group in the product molecule was 2 times of that of carboxyl, and the number of carbon-carbon double bonds was the same as that of the carboxyl.

Because the product had a carboxyl functional group in the molecule, the product comprised 2 aldehyde groups and 1 carbon-carbon double bond.

Figure 7:
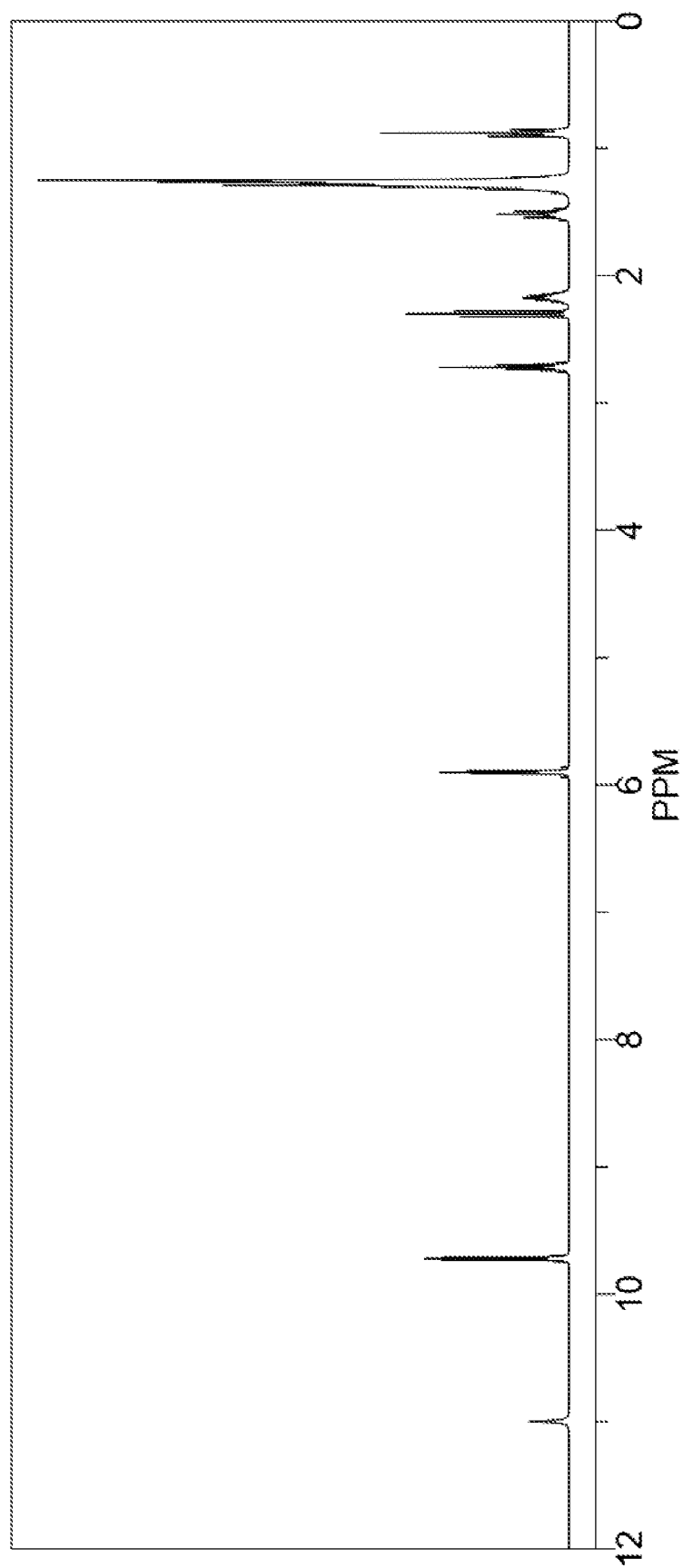
FIG. 7 illustrates the Hydrogen Nuclear Magnetic Resonance ($^1$H-NMR) spectrogram of the blockage inhibitor prepared in Example 1.

FIG. 7 illustrated the Hydrogen Nuclear Magnetic Resonance ($^1$H-NMR) spectrogram of the prepared blockage inhibitor, wherein the chemical shifts δ=9.7 ppm, δ=5.9 ppm, δ=2.7 ppm, δ=2.2 ppm, δ=1.3 ppm, δ=0.9 ppm were respectively assigned to

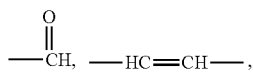

as well as

—CH$_2$— and —CH$_3$ under the different chemical environments, and it can be deduced that the structural formula of said product was a mixture of

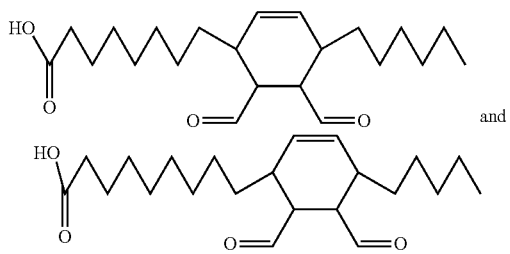

with reference to the splitting numbers.

As can be seen from the above spectrograms with reference to raw materials, an aliphatic ring structure and an aldehyde-based polar functional group had been successfully introduced into a molecular chain of the vegetable oil fatty acid through a modification reaction, the obtained blockage inhibitor product was exactly a mixture of the compounds with a structure represented by Formula (I), wherein x=0, y=0, m=5, n=7, R$_1$ and R$_2$ were each H, and x=0, y=0, m=4, n=8, and R$_1$ and R$_2$ were each H.

Example 2

(1) 1,000 g of corn oil, 2,500 g of ethylene glycol and 500 g of KOH were put into a reactor and uniformly mixed, and subjected to stirring and reaction at 180° C. for 3 hours, the product was acidified by hydrochloric acid until the pH was 2, and then washed with water to be neutral, the product was subjected to standing still and layering to separate out an aqueous phase, thereby obtaining the modified corn oil fatty acid.

(2) 100 g of modified corn oil fatty acid and 58.8 g of 2-butene dialdehyde were taken and added into an ultrasonic wave reactor, the compounds were subjected to stirring at 300 rpm and reaction for 2 h under the reaction temperature of 110° C. and the ultrasonic power of 100 W to finish the reaction; after the reaction system was cooled to room temperature, the reduced pressure distillation was performed, the fractions generated under the temperature of 200° C. and a pressure of 65 Pa were collected to obtain a blockage inhibitor product. The conversion rate of the corn oil fatty acid was 47.2%, the product had an acid value of 122.1 mgKOH/g and a condensation point of −26.3° C.

The Nuclear Magnetic Resonance, Infrared Spectroscopy, Gas Chromatography and TOF mass spectrometry showed that the product was exactly a mixture of the compounds with a structure represented by Formula (I), wherein x=0, y=0, m=5, n=7, R$_1$ and R$_2$ were each H, and x=0, y=0, m=4, n=8, and R$_1$ and R$_2$ were each H.

Example 3

(1) 1,000 g of corn oil, 3,000 g of ethylene glycol and 550 g of KOH were put into a reactor and uniformly mixed, and subjected to stirring and reaction at 170° C. for 4 hours, the product was acidified by hydrochloric acid until the pH was 3, and then washed with water to be neutral, the product was subjected to standing still and layering to separate out an aqueous phase, thereby obtaining the modified corn oil fatty acid.

(2) 100 g of modified corn oil fatty acid and 24.7 g of 2-butene dialdehyde were taken and added into an ultrasonic wave reactor, the compounds were subjected to stirring at 300 rpm and reaction for 0.5 h under the reaction temperature of 150° C. and the ultrasonic power of 300 W to finish the reaction; after the reaction system was cooled to room temperature, the reduced pressure distillation was performed, the fractions generated under the temperature of 200° C. and a pressure of 65 Pa were collected to obtain a blockage inhibitor product. The conversion rate of the corn oil fatty acid was 49.3%, the product had an acid value of 121.7 mgKOH/g and a condensation point of −27.0° C.

The Nuclear Magnetic Resonance, Infrared Spectroscopy, Gas Chromatography and TOF mass spectrometry showed that the product was exactly a mixture of the compounds with a structure represented by Formula (I), wherein x=0, y=0, m=5, n=7, R$_1$ and R$_2$ were each H, and x=0, y=0, m=4, n=8, and R$_1$ and R$_2$ were each H.

Example 4

The preparation process and operating conditions in Example 4 were the same as those in Example 1, except that cottonseed oil (with an iodine value of 108 mgKOH/g) was used as the starting material of reaction to obtain the blockage inhibitor product. The conversion rate of the cottonseed oil fatty acid was 45.3%, the product had an acid value of 122.4 mgKOH/g and a condensation point of −26.8° C.

The Nuclear Magnetic Resonance, Infrared Spectroscopy, Gas Chromatography and TOF mass spectrometry showed that the product was exactly a mixture of the compounds with a structure represented by Formula (I), wherein x=0, y=0, m=5, n=7, R$_1$ and R$_2$ were each H, and x=0, y=0, m=4, n=8, and R$_1$ and R$_2$ were each H.

Example 5

The preparation process and operating conditions in Example 5 were the same as those in Example 1, except that peanut oil (with an iodine value of 95 mgKOH/g) was used as the starting material of reaction to obtain the blockage inhibitor product. The conversion rate of the peanut oil fatty acid was 25.5%, the product had an acid value of 122.0 mgKOH/g and a condensation point of −26.8° C.

The Nuclear Magnetic Resonance, Infrared Spectroscopy, Gas Chromatography and TOF mass spectrometry showed that the product was exactly a mixture of the compounds with a structure represented by Formula (I), wherein x=0, y=0, m=5, n=7, R$_1$ and R$_2$ were each H, and x=0, y=0, m=4, n=8, and R$_1$ and R$_2$ were each H.

Example 6

The preparation process and operating conditions in Example 6 were the same as those in Example 1, except that shinyleaf yellowhorn oil (with an iodine value of 116 mgKOH/g) was used as the starting material of reaction to obtain the blockage inhibitor product. The conversion rate of the shinyleaf yellowhorn oil fatty acid was 39.5%, the product had an acid value of 122.2 mgKOH/g and a condensation point of −26.8° C.

The Nuclear Magnetic Resonance, Infrared Spectroscopy, Gas Chromatography and TOF mass spectrometry showed that the product was exactly a mixture of the compounds with a structure represented by Formula (I), wherein x=0, y=0, m=5, n=7, $R_1$ and $R_2$ were each H, and x=0, y=0, m=4, n=8, and $R_1$ and $R_2$ were each H.

Example 7

The preparation process and operating conditions in Example 7 were the same as those in Example 1, except that 50.8 g of 2-pentene dialdehyde was used as the starting material of reaction to obtain the blockage inhibitor product. The conversion rate of the corn oil fatty acid was 44.2%, the product had an acid value of 119.6 mgKOH/g and a condensation point of −25.8° C.

The Nuclear Magnetic Resonance, Infrared Spectroscopy, Gas Chromatography and TOF mass spectrometry showed that the product was exactly a mixture of the compounds with a structure represented by Formula (I), wherein x=0, y=1, m=5, n=7, $R_1$ and $R_2$ were each H, and x=0, y=1, m=4, n=8, and $R_1$ and $R_2$ were each H.

Example 8

The preparation process and operating conditions in Example 8 were the same as those in Example 1, except that 57.2 g of 3-hexene dialdehyde was used as the starting material of reaction to obtain the blockage inhibitor product. The conversion rate of the corn oil fatty acid was 42.5%, the product had an acid value of 117.4 mgKOH/g and a condensation point of −24.3° C.

The Nuclear Magnetic Resonance, Infrared Spectroscopy, Gas Chromatography and TOF mass spectrometry showed that the product was exactly a mixture of the compounds with a structure represented by Formula (I), wherein x=1, y=1, m=5, n=7, $R_1$ and $R_2$ were each H, and x=1, y=1, m=4, n=8, and $R_1$ and $R_2$ were each H.

Example 9

The preparation process and operating conditions in Example 9 were the same as those in Example 1, except that 70.0 g of 4-octene dialdehyde was used as the starting material of reaction to obtain the blockage inhibitor product. The conversion rate of the corn oil fatty acid was 30.5%, the product had an acid value of 115.7 mgKOH/g and a condensation point of −20.3° C.

The Nuclear Magnetic Resonance, Infrared Spectroscopy, Gas Chromatography and TOF mass spectrometry showed that the product was exactly a mixture of the compounds with a structure represented by Formula (I), wherein x=2, y=2, m=5, n=7, $R_1$ and $R_2$ were each H, and x=2, y=2, m=4, n=8, and $R_1$ and $R_2$ were each H.

Example 10

The preparation process and operating conditions in Example 10 were the same as those in Example 1, except that 1,3-propanediol was used for replacing ethylene glycol to obtain a blockage inhibitor product. The conversion rate of the corn oil fatty acid was 44.1%, the product had an acid value of 122.4 mgKOH/g and a condensation point of −26.3° C.

Example 11

The preparation process and operating conditions in Example 11 were the same as those in Example 1, except that 1,4-butanediol was used for replacing ethylene glycol to obtain a blockage inhibitor product. The conversion rate of the corn oil fatty acid was 40.2%, the product had an acid value of 122.2 mgKOH/g and a condensation point of −26.5° C.

Comparative Example 1

The preparation process and operating conditions in Comparative Example 1 were the same as those in Example 1, except that a blockage inhibitor was prepared by using the palm oil having an iodine value of 49 mgKOH/g as the starting material of the reaction. The conversion rate of the palm oil fatty acid was less than 6.4%, and the conversion rate of said blockage inhibitor was too low, so that the economic benefit was not generated.

Comparative Example 2

The preparation process and operating conditions in Comparative Example 2 were the same as those in Example 1, except that the vegetable oil and the unsaturated dialdehyde were directly used for reaction, but the product cannot be synthesized because the reaction was not performed.

Comparative Example 3

The preparation process and operating conditions in Comparative Example 3 were the same as those in Example 1, except that the tung oil with conjugated double bonds was used as the starting material of the reaction, the reaction system generated a cross-linking side reaction, the conversion rate of the tung oil fatty acid was 51.2%, and the condensation point of the product was −9° C. The condensation point was too high, such that the product did not meet the use requirement.

TABLE 1

| | | Vegetable oil | | | | | |
|---|---|---|---|---|---|---|---|
| | Fatty acid types | Corn oil | Cottonseed oil | Palm oil | Tung oil | Peanut oil | Shinyleaf yellowhorn oil |
| Fatty acid composition (%) | Palmitic acid | 10.9 | 21.6 | 42.2 | — | 10.8 | 10 |
| | Stearic acid | 2.0 | 2.6 | 1.6 | 4 | 2.8 | 2 |
| | Oleic acid | 25.4 | 18.6 | 37.3 | 8 | 42.5 | 31 |
| | Linoleic acid | 59.6 | 54.4 | 11.4 | 4 | 37.4 | 48 |
| | Linolenic acid | 0.6 | 0.7 | — | — | 0.1 | — |
| | α-eleostearic acid | — | — | — | 84 | — | — |

TABLE 1-continued

| | | Vegetable oil | | | | | |
|---|---|---|---|---|---|---|---|
| | Fatty acid types | Corn oil | Cottonseed oil | Palm oil | Tung oil | Peanut oil | Shinyleaf yellowhorn oil |
| Properties | Number of unsaturated double bonds | 4.5 | 3.9 | 2.2 | 7.5 | | |
| | Iodine values | 102-130 | 90-119 | 40-60 | 160-180 | 90-100 | 100-120 |

Test Example 1

The tests were carried out by using the low sulfur diesel (low sulfur diesel-1) having a sulfur content less than 10 ppm and the hydrorefined diesel (low sulfur diesel-2) having a wear scar diameter more than 580 μm, their specific properties were shown in Table 2. The blockage inhibitors prepared in the Examples and Comparative Examples were respectively added into the aforementioned low sulfur diesel to perform product performance tests, and the test results were shown in Table 3 and Table 4.

TABLE 2

| Types | low sulfur diesel-1 | low sulfur diesel-2 |
|---|---|---|
| Lubricity/μm | 588 | 684 |
| Viscosity (20° C.)/mm² · s⁻¹ | 4.37 | 4.24 |
| Acidity/mgKOH · 100 ml⁻¹ | <0.01 | <0.01 |
| Condensation point/° C. | −25 | −35 |
| Cold filtering point/° C. | −20 | −31 |
| Density/kg · m⁻³ | 817.0 | 805.0 |
| Tricyclic aromatic hydrocarbons/% | 0.1 | 0.1 |
| Total aromatic hydrocarbons/% | 8.5 | 4.2 |
| Sulfur content/ppm | 7 | 4 |
| Distillation range/° C.  50% | 275 | 264 |
| 90% | 305 | 301 |
| 95% | 310 | 315 |

TABLE 3

| Samples | Added amount/ ppm | Wear scar diameter/ μm | Whether to meet the lubricity requirement of national-V standard | Whether the modifying agent was precipitated at the temperature of −20° C. |
|---|---|---|---|---|
| low sulfur diesel-1 + corn oil | 80 ppm | 568 | No | Yes |
| low sulfur diesel-1 + product in step (1) of Example 1 | 80 ppm | 462 | No | Yes |
| low sulfur diesel-1 + cottonseed oil | 80 ppm | 569 | No | Yes |
| low sulfur diesel-1 + product in step (1) of Example 4 | 80 ppm | 464 | No | Yes |
| low sulfur diesel-1 + peanut oil | 80 ppm | 571 | No | Yes |
| low sulfur diesel-1 + product in step (1) of Example 5 | 80 ppm | 473 | No | Yes |
| low sulfur diesel-1 + shinyleaf yellowhorn oil | 80 ppm | 565 | No | Yes |
| low sulfur diesel-1 + product in step (1) of Example 6 | 80 ppm | 455 | Yes | Yes |

TABLE 3-continued

| Samples | Added amount/ ppm | Wear scar diameter/ μm | Whether to meet the lubricity requirement of national-V standard | Whether the modifying agent was precipitated at the temperature of −20° C. |
|---|---|---|---|---|
| low sulfur diesel-1 + Example 1 | 80 ppm | 373 | Yes | No |
| low sulfur diesel-1 + Example 2 | 80 ppm | 375 | Yes | No |
| low sulfur diesel-1 + Example 3 | 80 ppm | 380 | Yes | No |
| low sulfur diesel-1 + Example 4 | 80 ppm | 375 | Yes | No |
| low sulfur diesel-1 + Example 5 | 80 ppm | 371 | Yes | No |
| low sulfur diesel-1 + Example 6 | 80 ppm | 370 | Yes | No |
| low sulfur diesel-1 + Example 7 | 80 ppm | 345 | Yes | No |
| low sulfur diesel-1 + Example 8 | 80 ppm | 390 | Yes | No |
| low sulfur diesel-1 + Example 9 | 80 ppm | 404 | Yes | No |
| low sulfur diesel-1 + Example 10 | 80 ppm | 378 | Yes | No |
| low sulfur diesel-1 + Example 11 | 80 ppm | 386 | Yes | No |
| low sulfur diesel-1 + Comparative Example 3 | 80 ppm | 472 | No | Yes |

TABLE 4

| Samples | Added amount/ ppm | Wear scar diameter/ μm | Whether to meet the lubricity requirement of national-V standard | Whether the modifying agent was precipitated at the temperature of −30° C. |
|---|---|---|---|---|
| low sulfur diesel-2 + corn oil | 100 ppm | 652 | No | Yes |
| low sulfur diesel-2 + product in step (1) of Example 1 | 100 ppm | 476 | No | Yes |
| low sulfur diesel-2 + cottonseed oil | 100 ppm | 655 | No | Yes |
| low sulfur diesel-2 + product in step (1) of Example 4 | 100 ppm | 477 | No | Yes |
| low sulfur diesel-2 + peanut oil | 100 ppm | 658 | No | Yes |
| low sulfur diesel-2 + product in step (1) of Example 5 | 100 ppm | 484 | No | Yes |
| low sulfur diesel-2 + shinyleaf yellowhorn oil | 100 ppm | 637 | No | Yes |

TABLE 4-continued

| Samples | Added amount/ ppm | Wear scar diameter/ μm | Whether to meet the lubricity requirement of national-V standard | Whether the modifying agent was precipitated at the temperature of −30° C. |
|---|---|---|---|---|
| low sulfur diesel-2 + product in step (1) of Example 6 | 100 ppm | 458 | Yes | Yes |
| low sulfur diesel-2 + Example 1 | 100 ppm | 375 | Yes | No |
| low sulfur diesel-2 + Example 2 | 100 ppm | 366 | Yes | No |
| low sulfur diesel-2 + Example 3 | 100 ppm | 381 | Yes | No |
| low sulfur diesel-2 + Example 4 | 100 ppm | 378 | Yes | No |
| low sulfur diesel-2 + Example 5 | 100 ppm | 372 | Yes | No |
| low sulfur diesel-2 + Example 6 | 100 ppm | 371 | Yes | No |
| low sulfur diesel-2 + Example 7 | 100 ppm | 346 | Yes | No |
| low sulfur diesel-2 + Example 8 | 100 ppm | 393 | Yes | No |
| low sulfur diesel-2 + Example 9 | 100 ppm | 405 | Yes | No |
| low sulfur diesel-2 + Example 10 | 100 ppm | 382 | Yes | No |
| low sulfur diesel-2 + Example 11 | 100 ppm | 393 | Yes | No |
| low sulfur diesel-2 + Comparative Example 3 | 100 ppm | 476 | No | Yes |

As can be seen from Table 3 and Table 4, the lubricating effect of the low sulfur diesel was not desirable when the vegetable oil was directly adopted or the product of step (1) was adopted, the lubricity of the low sulfur diesel did not meet the diesel lubricity requirement of the national-V standard in China, and the modifying agent was precipitated at the temperature of −20° C. or −30° C. The vegetable oil fatty acid modified by the invention had obviously improved lubricity of the low sulfur diesel; when the added amount was 80 ppm or 100 ppm, the blended low sulfur diesel can meet the diesel lubricity requirement of national-V standard (the wear scar diameter was not more than 460 m), and there was not precipitation of said modifying agent at the temperature of −20° C. or −30° C. It demonstrated that the prepared blockage inhibitor product had obvious lubricating effect and low condensation point, and the used amount was small.

Test Example 2

In order to demonstrate that the product of the invention had the blockage inhibition property, 1 L of each low sulfur diesel-1 product was respectively taken and added with 20 mL of water, the mixture was violently shaken and then stored in an enclosed space, the total pollutants of the diesel samples whether adding the products of the Examples and the Comparative Examples were compared (the total pollutants mainly comprised bacteria generated in the diesel and excrement thereof, and the filter may be blocked due to excessively high content of the total pollutants), the detection of the total pollutants was determined according to the national standard GB/T33400 of China, and the results were shown in Table 5 as follows:

TABLE 5

| Samples | Added amount/ ppm | Total pollutants-detected after formulation/ ppm | Total pollutants-detected after standing still for 6 months/ppm |
|---|---|---|---|
| Diesel without adding the blockage inhibitor | — | 16.1 | 28.2 |
| low sulfur diesel-1 + Example 1 | 80 ppm | 16.2 | 16.4 |
| low sulfur diesel-1 + Example 2 | 80 ppm | 16.1 | 16.4 |
| low sulfur diesel-1 + Example 3 | 80 ppm | 16.2 | 16.5 |
| low sulfur diesel-1 + Example 4 | 80 ppm | 16.2 | 16.4 |
| low sulfur diesel-1 + Example 5 | 80 ppm | 16.3 | 16.4 |
| low sulfur diesel-1 + Example 6 | 80 ppm | 16.2 | 16.3 |
| low sulfur diesel-1 + Example 7 | 80 ppm | 16.2 | 16.6 |
| low sulfur diesel-1 + Example 8 | 80 ppm | 16.2 | 16.4 |
| low sulfur diesel-1 + Example 9 | 80 ppm | 16.2 | 16.4 |
| low sulfur diesel-1 + Example 10 | 80 ppm | 16.1 | 16.5 |
| low sulfur diesel-1 + Example 11 | 80 ppm | 16.2 | 16.5 |
| low sulfur diesel-1 + Comparative Example 3 | 80 ppm | 16.6 | 28.8 |

As can be seen from Table 5, the content of total pollutants in the diesel without adding the blockage inhibitor increased along with an extension of the standing time; the added product obviously improved the antibacterial property of the low sulfur diesel; when the addition amount was 80 ppm, the total pollutant content was basically kept unchanged after the blended low sulfur diesel was standing still for 6 months.

The invention claimed is:

1. A compound represented by Formula (I):

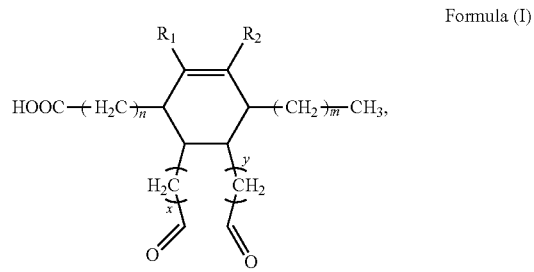

Formula (I)

wherein x and y are each an integer between 0 and 4; m and n are each an integer between 3 and 9, and 10≤m+n≤14; and $R_1$ and $R_2$ are independently chosen from H, a C1-C6 linear or branched alkyl group, or a C3-C6 cycloalkyl group.

2. The compound according to claim 1, wherein m is 4 or 5.

3. The compound according to claim 1, wherein x and y are each independently 0 or 1, or m+n=12, or both.

4. The compound according to claim 1, wherein $R_1$ and $R_2$ are independently chosen from H, methyl, or ethyl.

5. A method for preparing a vegetable oil based blockage inhibitor, wherein the method comprises the following steps:

(1) subjecting a non-conjugated vegetable oil to a haptoreaction with an alkali or an alcohol solution of an alkali under isomerization reaction condition;

(2) acidifying and washing a product obtained from the haptoreaction, and then separating out an aqueous phase to obtain a modified vegetable oil fatty acid;

(3) contacting the modified vegetable oil fatty acid with an unsaturated dialdehyde under Diels-Alder addition reaction condition to form a mixture; and (4) removing unreacted raw materials from the mixture obtained from step (3).

6. The method according to claim 5, wherein the non-conjugated vegetable oil of step (1) has non-conjugated carbon-carbon double bonds, a linolenic acid content of not more than 0.6%, and an iodine value of not less than 60 mgKOH/g.

7. The method according to claim 6, wherein the non-conjugated vegetable oil of step (1) has an iodine value of not less than 85 mgKOH/g.

8. The method according to claim 7, wherein the non-conjugated vegetable oil of step (1) is one or more selected from the group consisting of corn oil, cottonseed oil, peanut oil, sesame oil, and shinyleaf yellowhorn oil.

9. The method according to claim 5, wherein, in step (1), the akali is potassium hydroxide and/or sodium hydroxide at an amount of 0.5-0.6 times of the non-conjugated vegetable oil by mass; the alcohol is one or more selected from the group consisting of ethylene glycol, 1,3-propanediol, and 1,4-butanediol, and an amount of said alcohol is 2.5-3.5 times of the non-conjugated vegetable oil by mass.

10. The method according to claim 5, wherein the isomerization reaction condition in step (1) comprise a temperature of 180-220° C. and a duration of 3-5 hours.

11. The method according to claim 5, wherein the unsaturated dialdehyde in step (3) is one or more selected from the group consisting of 2-butene dialdehyde, 2-pentene dialdehyde, 2-hexene dialdehyde, 3-hexene dialdehyde, 2-heptene dialdehyde, 3-heptene dialdehyde, 2-octene dialdehyde, 3-octene dialdehyde, and 4-octene dialdehyde.

12. The method according to claim 5, wherein a molar ratio of unsaturated dialdehyde to vegetable oil fatty acid is 0.5:1-3:1.

13. The method according to claim 12, wherein the molar ratio of unsaturated dialdehyde to vegetable oil fatty acid is 0.8:1-2:1.

14. The method according to claim 5, wherein the Diels-Alder addition reaction condition of step (3) comprise a temperature of 190-210° C. and a time of 0.5-2 hours.

15. The method according to claim 5, wherein removing the unreacted raw materials in step (4) comprises subjecting the mixture obtained from step (3) to a reduced pressure distillation under a pressure of 30-150 Pa and a temperature of 180-220° C.

16. The method according to claim 15, wherein the reduced pressure distillation is carried out under a pressure of 65-120 Pa and a temperature of 195-205° C.

17. A low sulfur diesel blockage inhibitor composition comprising the compound according to claim 1.

18. The low sulfur diesel blockage inhibitor composition according to claim 17, wherein the low sulfur diesel blockage inhibitor composition comprises 70-90 wt % of vegetable oil based blockage inhibitor, 0.2-2 wt % of antioxidant, and 8-29 wt % of aromatic hydrocarbon solvent oil, based on the total amount of the low sulfur diesel blockage inhibitor composition.

19. A low sulfur diesel with improved blockage inhibition property, comprising a low sulfur diesel and a blockage inhibitor, wherein the blockage inhibitor is the compound according to claim 1.

20. The low sulfur diesel according to claim 19, wherein the content of said blockage inhibitor is 0.008-0.01 parts by weight relative to 100 parts by weight of the low sulfur diesel base oil.

* * * * *